US007879368B2

(12) United States Patent
Yusoff et al.

(10) Patent No.: US 7,879,368 B2
(45) Date of Patent: Feb. 1, 2011

(54) **PROCESS FOR PREPARATION OF *LABISIA PUMILA* EXTRACT**

(75) Inventors: Mashitah Mohd. Yusoff, Pahang (MY); Wan Nazaimoon Wan Mohamud, Kuala Lumpur (MY)

(73) Assignee: The Government of Malaysia as represented by the Ministry of Science, Technology and Innovation, Putrajaya (MY)

( * ) Notice: Subject to any disclaimer, the term of this patent is extended or adjusted under 35 U.S.C. 154(b) by 415 days.

(21) Appl. No.: 11/330,701

(22) Filed: Jan. 12, 2006

(65) Prior Publication Data
US 2007/0082069 A1   Apr. 12, 2007

(30) Foreign Application Priority Data
Oct. 12, 2005   (MY) ................................. PI20054784

(51) Int. Cl.
*A01N 65/00* (2009.01)
(52) U.S. Cl. ...................................... 424/725
(58) Field of Classification Search ........................ None
See application file for complete search history.

(56) References Cited

U.S. PATENT DOCUMENTS

2003/0203050 A1* 10/2003 Sherwood et al.

OTHER PUBLICATIONS

Fuad, Wem et al. Malaysian Journal of Medical Sciences (May 2005); 12(2): 13-21. Evaluation of th eteratogenicity of aqueous extract of *Labisisa pumila* var. alata in rats.*
The Malaysian Timber Council. http://www.borneofocus.com/saip/vaic/Natural_Wealth/kacip_fatimah.htm. "Kacip Fatimah". Downloaded Oct. 25, 2004.*
Internet Archive Wayback. http://web.archine.org/web/*/www.boreofocus.com/saip/vaic/Natural_Natural_Wealth/kacip_. WayBack Machine. Downloaded Oct. 25, 2007.*
Jamal Ja, et al. J Pharm. Pharmacol (1998), 50(Supplement): 79. Testing of *Labisia pumila* for oestrogenic activity using a recombinant yeast screen.*
Cech, R. Making Plant Medicine. Oregon: Horizon Herbs LLC, 2000. "Decoction", pp. 68-71.*
Jamal, Ja et al. 1999. Kacip Fatimah: A Malay Traditional Herb for Pregnant Women. In Phytochemicals and Biopharmaceutins from the Malaysian Rain Forest (A. Manaf Ali, Khozirah and Zuriati Zakaria, eds.). Kepong: FRIM, pp. 166-176.*
Cech, R. Making Plant Medicine. Oregon: Horizon Herbs LLC, 2000. "Decoction", pp. 68-71.*
Burkill, I.H. A Dictionary of the Economic Products of the Malay Peninsula. V. II (I-Z). Third print. Kuala Lumpur: Ministry of Agriculture. 1935. p. 1290.
Jaganath, I.B. et al. Herbs: The Green Pharmacy of Malaysia. Kuala Lumpur. MARDI and FRIM. 1999. pp. 53-54.
Jamal, J.A. et al. Kacip Fatimah: A Malay Traditional Herb for Pregnant Women. In Phytochemicals and Biopharmaceutins from the Malaysian Rain Forest (A. Manaf Ali, Khozirah Shaari and Zuriatia Zakaria, eds.). Kepong: FRIM. 1999. pp. 166-176.
Ismail, Z. et al. Malaysian Herbal Monograph. vol. I. Kuala Lumpur: Malaysian Herbal Monograph Committee. 1999. pp. 45-48.
Ismail, N. et al. Pharmacognosical Characterization of *Labisia pothoina*. In Trends in Traditional Medicine Research (Chan Kit Lam, Abas Hj. Hussin, Amirin Sadikun, Kah Hay Yuen, Mohd. Zaini Asmawi and Zhari Ismail, eds.). Pulau Pinang: Universiti Sains Malaysia. 1995. pp. 574-582.
Stone, B.C. Notes on the Genus Labisia Lindl. (Myrsinaceae). Malayan Nature Journal. 1988. 42:43-51.

* cited by examiner

*Primary Examiner*—Michele Flood
(74) *Attorney, Agent, or Firm*—Wolf, Greenfield & Sacks, P.C.

(57) ABSTRACT

A process for the preparation of *Labisia pumila* extract from *Labisia pumila* plant material and to obtain an optimized and reproducible chemical profile by high performance liquid chromatography.

7 Claims, 1 Drawing Sheet

PROCESS FOR PREPARATION OF *LABISIA PUMILA* EXTRACT

TECHNICAL FIELD OF THE INVENTION

The present invention relates generally to a process for preparation of plant extract and more particularly to the process for preparation of water-soluble *Labisia pumila* extract, and to obtain a reproducible chemical profile by reverse-phase high performance liquid chromatography (HPLC).

BACKGROUND OF THE INVENTION

Traditional Malay medicine dictates that "kacip fatimah" (or Selusoh fatimah, Rumput siti fatimah, Akar fatimah, Kachit fatimah, Kachip fatimah, Kachip patimah, Kunchi fatimah, Pokok pinggang, Rumput palis, Tadah mata hari, Mata pelandok rimba, Bunga belangkas hutan), as disclosed in Burkhill (1993) is used much in childbirth. A detection of the plant is given not only after childbirth as a protective medicine, but before to expedite labour. Additional uses include being given for flatulence, dysentery, dysmenorrhoea, gonorrhoea and "sickness in the bones".

While there is now an increasing demand for the supply of "kacip fatimah" (*Labisia pumila* syn. *Labisia pothoina*) in the food industries, the reproducibility of extraction processes is still in doubt due to the lack of reliable chemical profiling methods.

SUMMARY OF THE INVENTION

Accordingly, it is the primary object of the present invention to provide a process for the preparation of a water-soluble *Labisia pumila* extract from *Labisia pumila* plant material.

It is another object of the present invention to provide a method for isolating a marker compound from water-soluble *Labisia pumila* extract by reverse-phase high performance liquid chromatography (HPLC).

It is yet another object of the present invention to provide structural elucidation of the marker compound obtained from the water-soluble *Labisia pumila* extract by nuclear magnetic resonance (nmr) spectrometry, liquid chromatography mass spectrometry (lcms) and ultraviolet (uv) spectrophotometry.

These and other objects of the present invention are accomplished by providing,

A process for preparation of *Labisia pumila* extract by extracting dried *Labisia pumila* material with water to form a water-soluble extract and drying the extract obtained, characterized in that the ratio of dried *Labisia pumila* plant material:water is 1:6.

and

A process for obtaining optimized and reproducible chemical profile of *Labisia pumila* extract comprising the steps of
a) centrifuging a mixture of water and dried extract obtained by extracting dried *Labisia pumila* plant material with water in a ratio of 1:6 of dried *Labisia pumila* plant material:water to form a water-soluble extract and drying the extract; optionally drying at a temperature of 40° C. for 3 days; optionally wherein the extraction process is carried out at 80° C. for 3 hours and with continuous stirring; optionally wherein the extraction process is repeated and the ratio of *Labisia pumila* plant material:water is 1:6; optionally wherein the *Labisia pumila* extract is dried and concentrated by spray-drying; optionally wherein the spray-drying is performed using a spray tower having a tower inlet and outlet, and wherein tower inlet temperature is 185° C. and wherein tower outlet temperature is 107° C., respectively.
b) diluting the supernatant obtained from (a) to 10 ml, with shaking;
c) filtering the diluted supernatant obtained in (b) with a 0.45 µm PTFE membrane filter; and
d) subjecting the filtered supernatant obtained in (c) to high performance liquid chromatography analysis.

and

A process for isolating a marker compound by semi-preparative reverse-phase high performance liquid chromatography from *Labisia pumila* extract obtained by extracting dried *Labisia pumila* plant material with water in a ratio of 1:6 of dried *Labisia pumila* plant material:water to form a water-soluble extract and drying the extract; optionally drying at a temperature of 40° C. for 3 days; optionally wherein the extraction process is carried out at 80° C. for 3 hours and with continuous stirring; optionally wherein the extraction process is repeated and the ratio of *Labisia pumila* plant material:water is 1:6; optionally wherein the *Labisia pumila* extract is dried and concentrated by spray-drying; optionally wherein the spray-drying is performed using a spray tower having a tower inlet and outlet, and wherein tower inlet temperature is 185° C. and wherein tower outlet temperature is 107° C., respectively.

and

A process for elucidating the structure of a marker compound by any one of nuclear magnetic resonance spectrometry, liquid chromatography mass spectrometry and ultraviolet spectrophotometry from *Labisia pumila* extract obtained by extracting dried *Labisia pumila* plant material with water in a ratio of 1:6 of dried *Labisia pumila* plant material:water to form a water-soluble extract and drying the extract; optionally drying at a temperature of 40° C. for 3 days; optionally wherein the extraction process is carried out at 80° C. for 3 hours and with continuous stirring; optionally wherein the extraction process is repeated and the ratio of *Labisia pumila* plant material:water is 1:6; optionally wherein the *Labisia pumila* extract is dried and concentrated by spray-drying; optionally wherein the spray-drying is performed using a spray tower having a tower inlet and outlet, and wherein tower inlet temperature is 185° C. and wherein tower outlet temperature is 107° C., respectively.

The present invention relates to a process for the preparation of a water-soluble *Labisia pumila* extract from *Labisia pumila* plant material. When considering the potential utilization of *Labisia pumila* in food products, medicines, etc., the safety of its use is considered as the solvent used in the process of the present invention is water.

DETAILED DESCRIPTION OF THE INVENTION

Figure 1:
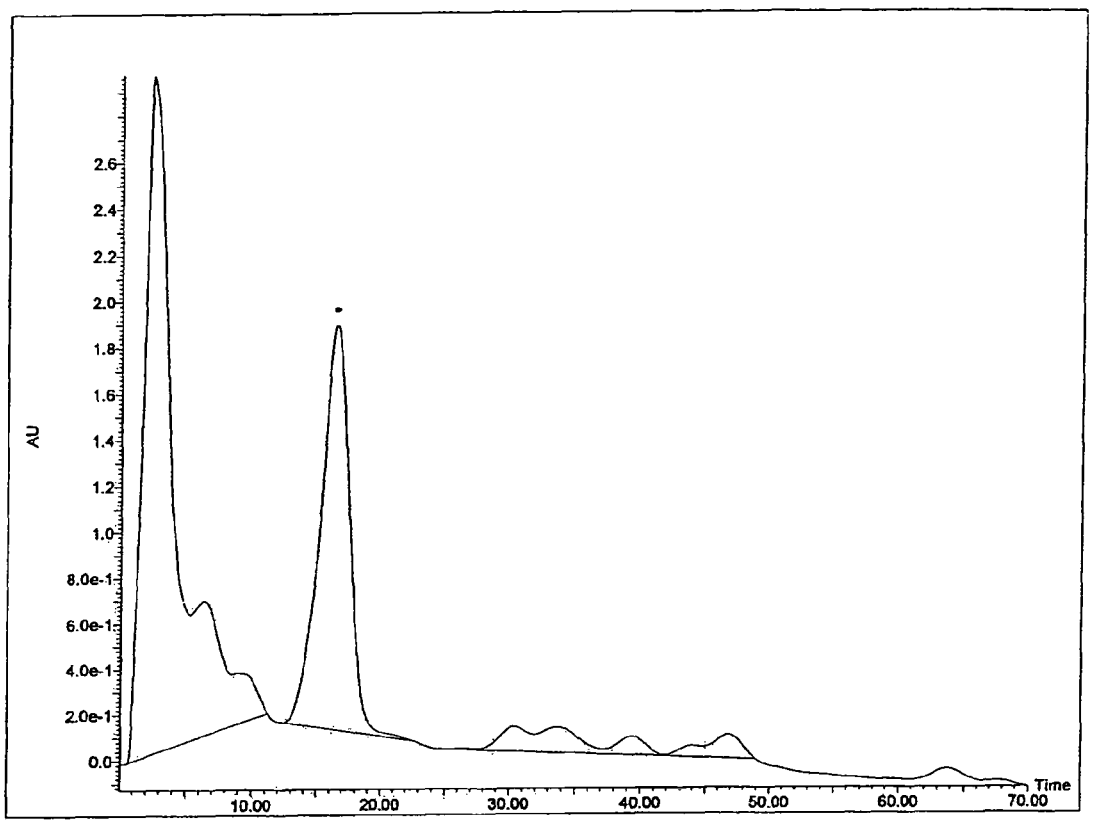
FIG. 1 shows a typical chromatogram of the *Labisia pumila* reverse-phase HPLC profile. The asterisk (*) indicates the marker compound.

The present invention relates to a process for preparation of a water-soluble *Labisia pumila* extract from *Labisia pumila* plant material and to obtain an optimized and reproducible chemical profile by reverse-phase high performance liquid chromatography.

Typically, the present invention which is a process for preparation of a water-soluble *Labisia pumila* extract comprises the following steps (1)-(4):

Step 1: extracting *Labisia pumila* dried plant material with a solvent (water) to form a water-soluble extract and concentrating the extract to dryness;

Step 2: subjecting the dried concentrated water-soluble *Labisia pumila* extract to reverse-phase high performance liquid chromatography (HPLC) analysis to obtain an optimized and reproducible chemical profile;

Step 3: isolating a marker compound from the water-soluble *Labisia pumila* extract by chromatographic method consisting of reverse-phase high performance liquid chromatography (HPLC); and Step 4: elucidating the structure of the marker compound obtained from the water-soluble *Labisia pumila* extract by nuclear magnetic resonance (nmr) spectrometry, liquid chromatography mass spectrometry (lcms) and ultraviolet (uv) spectrophotometry.

As mentioned above, the process for preparation of a water-soluble *Labisia pumila* extract according to the present invention, describes the method for obtaining a water-soluble *Labisia pumila* extract by extracting *Labisia pumila* dried plant material with a solvent (water) to form a water-soluble extract and concentrating the extract to dryness; and subjecting the dried concentrated water-soluble *Labisia pumila* extract to reverse-phase high performance liquid chromatography (HPLC) analysis to obtain an optimized and reproducible chemical profile. By utilizing this process it is possible to successfully provide a process for preparing water-soluble *Labisia pumila* extract that is consistently reproducible.

The process also follows a time-tested process of preparing *Labisia pumila* extract by traditional Malay medicine practitioners, albeit, on a smaller scale, for individual consumption. The process of the present invention can therefore yield the desired extract that is free from introduced chemical impurities and is reproducible.

Process for Preparation of Water-soluble *Labisia pumila* Extract

Starting Material

In the process for the preparation of water-soluble *Labisia pumila* extract according to the present invention, the starting material must be *Labisia pumila* plant material. In the present invention, only *Labisia pumila* plant material may be used as the starting material.

The starting material is fully dehydrated by drying at 40° C. for 3 days before use so that it will not be affected by the polarity of a solvent.

The above-described starting material may be used as the starting material in the present invention in any form, for example, solid powder, or minced form, or even in the form of any combination of these forms.

Extraction

A conventional method is used to prepare a water-soluble *Labisia pumila* extract. In the present invention, it is preferable to use a solvent extraction method, which is most frequently used these days.

Using the solvent extraction method, it is possible to fully extract *Labisia pumila*, which is necessary in the process of the invention.

A solvent typically used for this solvent extraction method is a non-polar solvent. In the present invention, water (a polar solvent) is used to adhere to a time-tested traditional Malay practice of extracting *Labisia pumila*. Moreover, it has been used as an extraction solvent in the food industry, and is thus highly safe.

The method for extracting *Labisia pumila* is effected by means of extraction at approximately 80° C., in order to attain increased efficiency of extraction. This extraction is conducted over a period of 3 hours and with continuous stirring. This extraction is repeated with an equal volume of fresh solvent, i.e., a two-stage process, in the ratio of one part dried plant material and six parts water.

Concentration of Extract to Dryness

A conventional method is used to dry the extract that has been obtained from the starting material to dryness.

Typical examples of methods of concentration include concentration under reduced pressure, concentration by heating, through-flow concentration, freeze concentration, and spray concentration, and these methods may be used either singly or in combination. In the present invention, spray-drying is preferably used. The tower inlet and outlet temperatures are set at 185° C. and 107° C., respectively. It is a simple and inexpensive method for removing the solvent that has been used for drying the extracted starting material.

EXAMPLE 1

In one embodiment, 100 kg of *Labisia pumila* dried and ground plant material is subjected to extraction by heating in 600 L of water at 80° C. over a period of 3 hours and with continuous stirring. The solvent is replaced with an equal volume of fresh solvent at the end of the extracting period and the plant material re-extracted. The mixtures are pooled together, then filtered and filtrate subjected to spray drying. The spray tower conditions are as follows; tower inlet and outlet temperatures are set at 185° C. and 107° C., respectively. The yield of water-soluble extract powder is 4-5%.

EXAMPLE 2

In another embodiment, 150 kg of *Labisia pumila* dried and ground plant material is subjected to extraction by heating in 900 L of water at 80° C. over a period of 6 hours and with continuous stirring. The solvent is replaced with an equal volume of fresh solvent at the end of the extracting period and the plant material re-extracted. The mixtures are pooled together, then filtered and filtrate subjected to spray drying. The spray tower conditions are as follows; tower inlet and outlet temperatures are set at 185° C. and 107° C., respectively. The yield of water-soluble extract powder is 4-5%.

Chemical Profiling

A conventional method is used to profile the extract which is water-soluble, chemically.

In the present invention, reverse-phase high performance liquid chromatography (HPLC) is typically used, and a conventional detector, for example, an ultraviolet, diode array or photodiode array detector (wavelength set at 254 nm) can be used for detection.

By conducting reverse-phase high performance liquid chromatography, it is possible to chemically profile the water-soluble extract. In the present invention, the chemical profiling method used is reproducible.

Typically, to prepare a sample for chemical profiling, the dried extract is accurately weighed and approximately 35-45 mg and centrifuged in exactly 10 ml of water at 20,000 rpm and room temperature for 15 minutes. Upon completion, the supernatant is transferred into a 10-mL volumetric flask, diluted to the mark with water, shaken for 15 minutes and then filtered with a 0.45 μm PTFE membrane filter.

Typically, a reference solution is also prepared in a similar manner. The solution is further serially diluted and used to construct a three or five point calibration curve.

High performance liquid chromatography (HPLC) system parameters are set as below:

| Column | stationary phase: octadecylsilyl silica gel for reverse-phase chromatography |
| --- | --- |
|  | 250 mm × 4.6 mm, 120 Å dp = 4 μm |
| Mobile Phase | A = $CH_3CN$; B = $H_2O$ (0.25% $H_3PO_4$) |
| Solvent System | A/B = 1/99 |
| Flow Rate | 1 ml/min |
| Temperature | Ambient |
| Wavelength Detection | 254 nm |
| Sample Size | 50 μL |

A typical chromatogram of the *Labisia pumila* reverse-phase HPLC profile is shown in FIG. 1. The asterisk (*) indicates the marker compound.

The chemical compound used as a marker for the extract typically appears as a single peak absorbing at 254 nm between 15 to 17 minutes in the HPLC profile or chromatogram.

The chemical compound used as a marker is typically 35-45 μg/ml as quantified by HPLC.

The marker compound analyzed and quantified from the water-soluble *Labisia pumila* extract was isolated, structurally elucidated and identified by means of comparison with a known standard reference.

Isolation of Chemical Marker

A conventional method used to isolate the marker compound from the water-soluble *Labisia pumila* extract by chromatographic method consists of semi-preparative or preparative reverse-phase high performance liquid chromatography (HPLC).

High performance liquid chromatography (HPLC) system parameters are set as below:

| Solvent System | Isocratic, 99% (0.1% $H_3PO_4$):1% ($CH_3CN$) |
| --- | --- |
| Temperature | Ambient |
| Wavelength Detection | 254 nm |

Typically, the marker compound is collected as a pure fraction at retention times between 15 minutes to 17 minutes.

Typically, the marker compound dried in vacuum is a brown powder, sparingly soluble in hydrophilic solvents.

Structure Elucidation of Chemical Marker

Typically, elucidating the structure of the marker compound involves nuclear magnetic resonance (nmr) spectrometry, liquid chromatography mass spectrometry (lcms) and ultraviolet (uv) spectrophotometry.

Typically the marker compound will give an M-1 ion at m/z 169.2 using negative ion APCI in liquid chromatography mass spectrometry (lcms), thus indicating a molecular weight of 170 which is compatible with the empirical formula $C_7H_6O_5$. Ions at 168 and 125 are indicative of the loss of H and COOH and suggest the presence of a carboxylic acid.

Typically the marker compound will give a single maximum at approximately 270 nm in ultraviolet (uv), suggesting a simple aromatic ring.

Typically the marker compound run in nuclear magnetic resonance (nmr) using deuterated dimethyl sulfoxide (DMSO-$d_6$) as solvent gives a proton ($^1H$) spectrum with the following resonances; a single signal for proton(s) bonded to carbon at δ 6.92 and broad signals between δ 9 and 10 attributed to protons attached to oxygen.

Typically the marker compound run in nuclear magnetic resonance using deuterated dimethyl sulfoxide (DMSO-$d_6$) as solvent gives a carbon ($^{13}C$) spectrum with the following resonances; δ167.4 (1C, carboxylic acid), 145.4 (2C, aromatic carbons attached to oxygen and with an oxygen on an adjacent carbon), 138.0 (1C, aromatic carbon attached to oxygen and with oxygens also attached to both adjacent carbons), 120.4 (aromatic carbon), 108.7 (2C, methane (CH) aromatic carbons). Also typically, the doubling of resonances at δ 145.4 and 108.7 required the molecule to be symmetrical and that the resonances at δ 145.4 and 138.0 required three adjacent aromatic carbons be oxygenated.

The identity of the marker compound isolated and structurally elucidated, was further verified by means of comparison with a known standard reference. As such the structure of the compound is determined to be 3,4,5-trihydroxybenzoic acid, as follows:

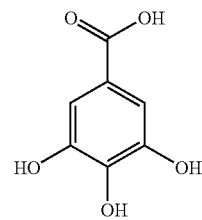

Thus, by using the process as described in the present invention, highly concentrated herbal extracts, especially of *Labisia pumila*, can be obtained easily and inexpensively from starting material consisting of *Labisia pumila*. The *Labisia pumila* extract obtained by the process of the present invention can be supplied in large quantities as starting material for the medicinal, pharmaceutical and food industries, in which the supply of *Labisia pumila* is now in high demand. Further, the *Labisia pumila* obtained by the process of the present invention can be used as starting material for producing individual pharmacologically active chemical compounds in the future.

Although the present invention has been described above with respect to various presently preferred embodiments, it will be apparent to one of ordinary skill in the art that many variations and modifications may be made. Therefore, the invention is not to be understood as limited to the particular embodiments recited herein but, rather, is to be understood as embracing all such variations and modifications which fall within the spirit and scope of the claims appended hereto.

All references disclosed herein are incorporated by reference in their entirety.

REFERENCES

Burkill, I. H. 1993. A Dictionary of the Economic Products of the Malay Peninsula. v. II (I-Z). Third print. Kuala Lumpur: Ministry of Agriculture. 1311.

Indu Bala Jaganath and Lean Teik Ng. 1999. Herbs: The Green Pharmacy of Malaysia. Kuala Lumpur: MARDI and FRIM. 53-54.

Jamia A. Jamal, Peter J. Houghton and Stuart R. Milligan. 1999. Kacip Fatimah: A Malay Traditional Herb for Pregnant Women. In Phytochemicals and Biopharmaceutins from the Malaysian Rain Forest (A. Manaf Ali, Khozirah Shaari and Zuriati Zakaria, eds.). Kepong: FRIM. 166-176

Malaysian Herbal Monograph. Vol. I. Kuala Lumpur: Malaysian Herbal Monograph Committee. 45-48.

Norhayati Ismail, Muzlifah Abd. Manaf and Zhari Ismail. Pharmacognosical Characterization of *Labisia pothoina*. In Trends in Traditional Medicine Research (Chan Kit Lam, Abas Hj. Hussin, Amirin Sadikun, Kah Hay Yuen, Mohd. Zaini Asmawi and Zhari Ismail, eds.). Pulau Pinang: Universiti Sains Malaysia. 574-582

Benjamin C. Stone. 1988. Notes on the Genus Labisia Lindl. (Myrsinaceae). Malayan Nature Journal. 42: 43-51

The invention claimed is:

1. A process for preparation of *Labisia pumila* extract by extracting dried *Labisia pumila* plant material with water at a ratio of 1:6 of dried *Labisia pumila* plant material:water to form a water-soluble extract and drying the extract wherein the extracting is carried out at 80° C. for 3 hours and with continuous stirring.

2. The process according to claim 1, wherein the dried *Labisia pumila* plant material is prepared by drying at a temperature of 40° C. for 3 days.

3. The process according to claim 1, wherein the extracting is repeated and the ratio of *Labisia pumila* plant material:water is 1:6.

4. The process according to claim 1, wherein the drying of the *Labisia pumila* extract is dried by spray-drying; and, wherein the spray-drying comprises concentrating and drying.

5. The process according to claim 4, wherein the spray-drying is performed using a spray tower having a tower inlet and outlet, and wherein tower inlet temperature is 185° C. and wherein tower outlet temperature is 107° C., respectively.

6. The process according to claim 1, wherein the extract comprises a marker compound.

7. The process according to claim 6, wherein the marker compound is 3,4,5-trihydroxybenzoic acid.

* * * * *